(12) United States Patent
Levy

(10) Patent No.: US 6,749,600 B1
(45) Date of Patent: Jun. 15, 2004

(54) BRAIDED SPLITTABLE CATHETER SHEATH

(75) Inventor: Tamir Levy, Ein HaEmek (IL)

(73) Assignee: Impulse Dynamics N.V., Curacao (AN)

( * ) Notice: Subject to any disclaimer, the term of this patent is extended or adjusted under 35 U.S.C. 154(b) by 0 days.

(21) Appl. No.: 09/713,538

(22) Filed: Nov. 15, 2000

(51) Int. Cl.⁷ .......................... A61M 25/00; A61F 11/00
(52) U.S. Cl. .................... 604/527; 606/108; 604/324
(58) Field of Search .................. 604/164.05, 522–528; 606/192, 108; 600/114

(56) References Cited

U.S. PATENT DOCUMENTS

| 4,581,025 A | | 4/1986 | Timmermans |
| 4,899,787 A | * | 2/1990 | Ouchi et al. ............... 138/131 |
| 4,921,479 A | | 5/1990 | Grayzel |
| 5,057,092 A | | 10/1991 | Webster |
| 5,713,867 A | * | 2/1998 | Morris ............... 604/164.05 |
| 5,957,903 A | * | 9/1999 | Mirzaee et al. ............ 604/524 |

OTHER PUBLICATIONS

Bencini et al, Steerable device for introducing diagnostic and therapeutic apparatus into the body. US Patent Pub. No. 2003/0135156 A1, Jul. 17, 2003.*

* cited by examiner

Primary Examiner—Brian L. Casler
Assistant Examiner—Roz Maiorino
(74) Attorney, Agent, or Firm—William H. Dippert; Reed Smith LLP

(57) ABSTRACT

Apparatus is provided for insertion into a lumen of a body of a subject. The apparatus includes a sheath, the sheath including at least one section which is reinforced by braiding. The section extends longitudinally along at least a portion of the sheath. The sheath also includes at least one section which is substantially not reinforced, which extends longitudinally along at least the portion.

5 Claims, 3 Drawing Sheets

BRAIDED SPLITTABLE CATHETER SHEATH

FIELD OF THE INVENTION

The present invention relates generally to invasive apparatus and methods for treating a patient, and specifically to facilitation of percutaneous insertion of devices into a patient's body.

BACKGROUND OF THE INVENTION

The use of catheters to inject, sample, drain, biopsy and implant various instruments in a body has developed into a highly sophisticated area of medical and veterinary practice. Seldinger, for example, developed a commonly-used technique for introducing a catheter into the vascular system of a patient. The equipment required to perform this basic technique includes a thin wall introducer needle, a wire guide, and a plastic preformed catheter. A simple puncture is performed, in conjunction with x-ray films for guidance, and access is gained to any part of the body via the cardiovascular system.

U.S. Pat. No. 4,581,025 to Timmermans, which is incorporated herein by reference, describes the use of a longitudinally-split catheter, which allows easy removal of the sheath from a patient's body.

U.S. Pat. No. 4,921,479, to Grayzel, which is incorporated herein by reference, describes a catheter sheath with a longitudinal seam. The seam includes a longitudinal slit, which allows enlargement of the sheath's diameter to accommodate a catheter inserted therein. It further allows the wall of the sheath to fit snugly around the catheter to afford guidance of the catheter into a blood vessel.

U.S. Pat. No. 5,057,092 to Webster, which is incorporated herein by reference, describes a catheter sheath, having a flexible plastic inner wall and a braided reinforcing mesh surrounding the inner wall. The reinforcing mesh allows the catheter sheath to be thinner than would be possible using, for example, the catheter described in the Timmermans patent, because a non-reinforced, thin-walled catheter would be likely to tear in some circumstances. Nevertheless, the catheter sheath described in the Webster patent is relatively difficult to remove from the patient's body.

In general, the current state of the art appears to have the disadvantage of either having relatively weak, easily torn and easily removable thin-walled catheter sheaths, somewhat stronger, bulkier, thick-walled sheaths that are easily removable, or reinforced thin-walled sheaths, which are relatively difficult to remove from the body.

SUMMARY OF THE INVENTION

It is an object of some aspects of the present invention to provide improved methods and apparatus for inserting a catheter sheath into a patient's body.

It is a further object of some aspects of the present invention to provide improved methods and apparatus for removing a catheter sheath from a patient's body.

In preferred embodiments of the present invention, a partially-braided sheath has one or more longitudinal sections. A physician typically inserts the sheath into a vessel of a patient, and guides a catheter through the sheath to a destination inside the patient's body. For some applications, the physician then withdraws the sheath from the vessel, while generally maintaining the catheter in place. Preferably, there are one or more respective seams between adjacent edges of the sections of the sheath, which bind the sections together prior to and during use of the sheath. Each of the seams preferably comprises a longitudinal slit, which enables the sheath to be easily split by the physician, upon removal of the sheath from the body.

Advantageously, the partial braiding of the sheath typically increases the resistance to kinking and overall mechanical strength thereof, such that insertion of the sheath into the vessel is relatively easy. By contrast, the prior art describes two major classes of catheter systems. The first class includes a reinforced and easily-inserted sheath, which is relatively difficult to remove from the body, such as that described in the above-cited U.S. Pat. No. 5,057,092. The second class includes a relatively soft and flexible sheath, which is difficult to insert, but has a longitudinal slit to make the sheath easy to remove, as described in the above-cited U.S. Pat. No. 4,921,479. Preferred embodiments of the invention described herein combine the advantages of both types of prior art catheter sheaths, yet minimize the disadvantages of each type of prior art sheath. The braiding of parts of the catheter sheath adds mechanical strength so as to allow easy insertion of a thin-walled sheath which is unlikely to tear, while the one or more longitudinal seams allow easy splitting of the sheath upon its removal from the vessel.

There is therefore provided, in accordance with a preferred embodiment of the present invention, apparatus for insertion into a lumen of a body of a subject, including a sheath, the sheath including:

at least one section which is reinforced by braiding, the section extending longitudinally along at least a portion of the sheath; and at least one section which is substantially not reinforced, extending longitudinally along at least the portion.

Preferably, the at least one section which is substantially not reinforced includes a seam, which is adapted to open responsive to application of lateral tension thereto.

For some applications, the sheath is adapted to be inserted into a blood vessel.

There is also provided, in accordance with a preferred embodiment of the present invention, a method for removing a sheath from a lumen of a body of a subject, including:

withdrawing the sheath from the lumen so that a segment of the sheath is outside the body, the sheath having at least one longitudinal section thereof which is reinforced by braiding, and at least one longitudinal section thereof which is substantially not reinforced; and applying tension to the non-reinforced section, so as to split the sheath longitudinally at the non-reinforced section.

Preferably, applying the tension so as to split the sheath includes splitting the sheath along a seam of the at least one longitudinal section which is substantially not reinforced.

The present invention will be more fully understood from the following detailed description of the preferred embodiments thereof, taken together with the drawings, in which:

DETAILED DESCRIPTION OF PREFERRED EMBODIMENTS

Figure 1:
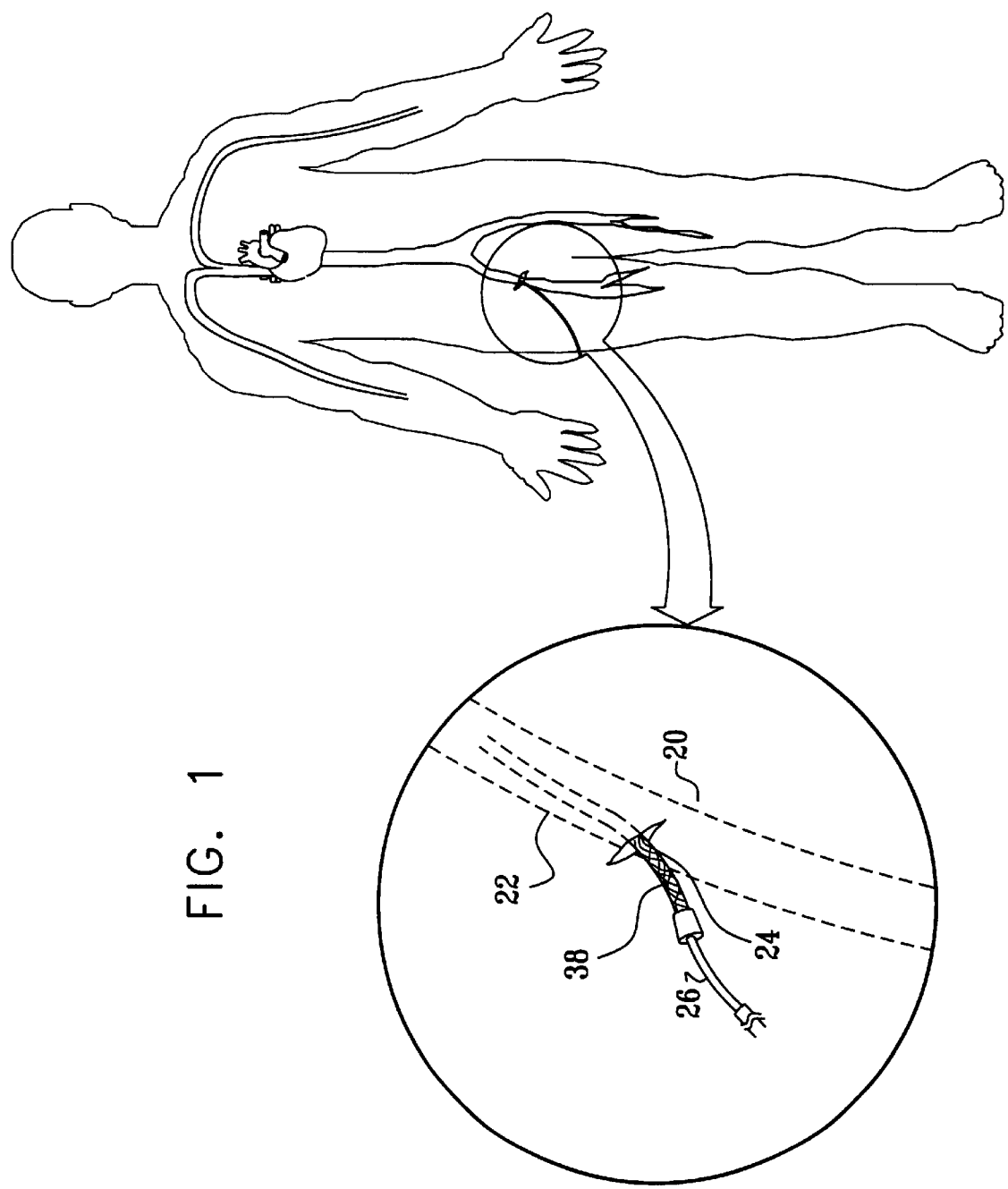
FIG. 1 is a simplified pictorial illustration showing the introduction of a catheter and a sheath into a patient's body, in accordance with a preferred embodiment of the present invention.

FIG. 1 is a pictorial illustration showing the placement of an introducer sheath 24 and a catheter 26 into a vessel 22 of a patient's body, in accordance with a preferred embodiment of the present invention. Vessel 22 may be a blood-carrying vessel, such as an artery or a vein, a urinary vessel, or substantially any body lumen into which it is known in the art to place a catheter. Introducer sheath 24 is typically inserted into vessel 22, and, thereafter, catheter 26 is passed through sheath 24. Alternatively, sheath 24 and catheter 26 are introduced simultaneously. Sheath 24 typically comprises one or more longitudinally-oriented braided sections 38, which increase the mechanical strength of sheath 24, as well as one or more non-braided sections (not shown), described with reference to FIGS. 2A, 2B, and 3 hereinbelow.

Figure 2A:
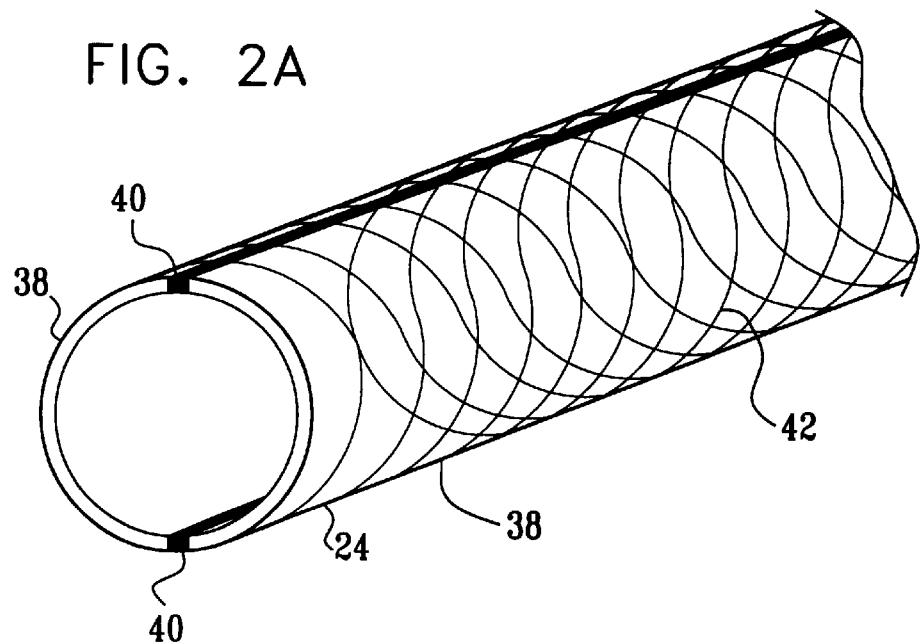
FIG. 2A is a schematic illustration showing a partially-braided sheath, in accordance with a preferred embodiment of the present invention.
Figure 2B:
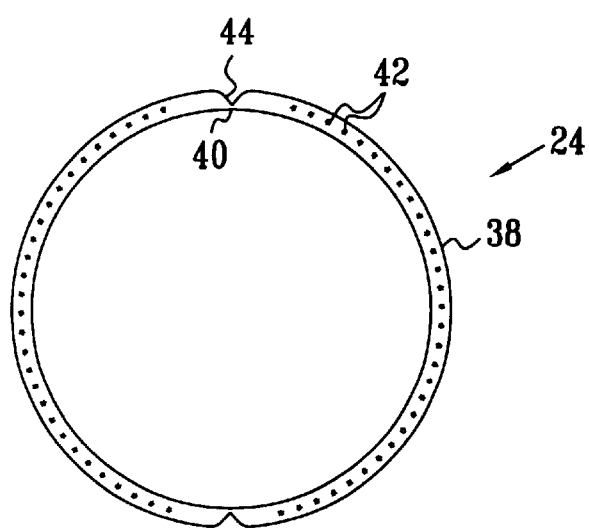
FIG. 2B is a schematic illustration showing a cross-sectional view of the sheath of FIG. 2A, in accordance with a preferred embodiment of the present invention.

Reference is now made to FIGS. 2A and 2B. FIG. 2A is a schematic illustration showing sheath 24, including two longitudinal braided sections 38 and two longitudinal non-braided sections 40, disposed between sections 38, in accordance with a preferred embodiment of the present invention. FIG. 2B is a schematic illustration showing a cross-sectional view of sheath 24, in accordance with a preferred embodiment of the present invention. Braided sections 38 typically comprise braiding elements 42, which reinforce the mechanical strength of the sections for part or all of their lengths. Non-braided sections 40 typically each comprise a seam 44, which may include a thinned region (such as in FIG. 2B) or a perforated slit (not shown) running along the length of the sheath. It is noted that the thinned region, as well as sheath 24 in general, can be easily produced using standard apparatus and polymer-extrusion processes known in the art. Preferably, but not necessarily, braiding elements 42 are generally sinusoidal in shape, and oscillate from the edge of one of the seams to the edge of the other seam, along the length of sheath 24. Further preferably, the braiding elements are introduced into the sheath during formation of the sheath.

Figure 3:
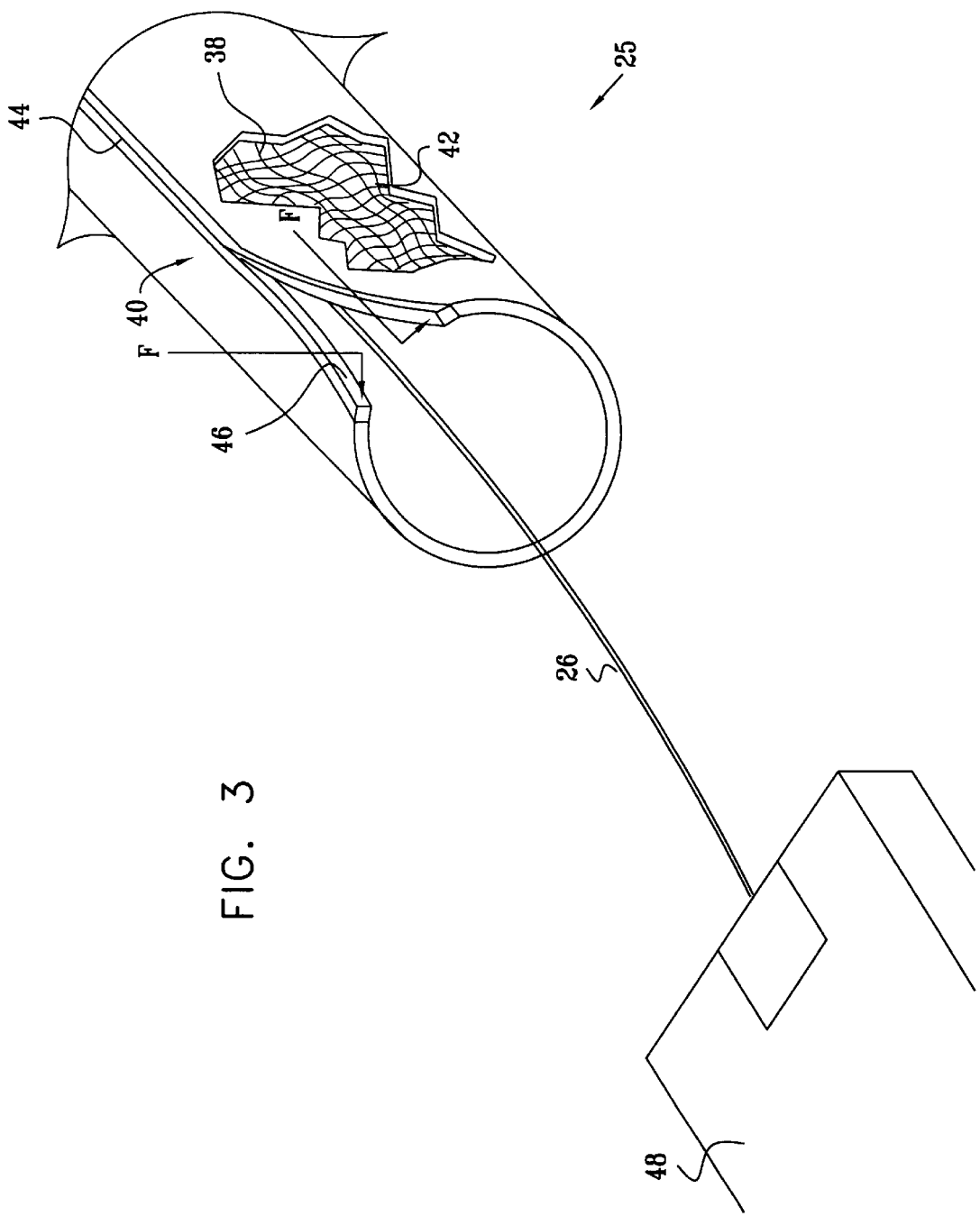
FIG. 3 is a schematic illustration showing a partially-braided sheath in use, in accordance with a preferred embodiment of the present invention.

FIG. 3 is a schematic illustration showing a sheath 25, including a single longitudinal non-braided section 40 and a single braided section 38, in accordance with a preferred embodiment of the present invention. For most applications, catheter 26 is coupled to external apparatus 48, which may include electronics or other means for controlling or otherwise interacting with the distal end of catheter 26. It is noted that prior art braided sheaths are difficult to remove from a patient's body, because the external apparatus used with the prior art sheaths is typically significantly larger than the inner diameter of the sheaths, and therefore blocks the removal thereof from the patient's body. These prior art sheaths, which are braided around their entire circumference (as is common with reinforced tubing), are strong but are not easy to split. Sheath 25, by contrast, is essentially just as strong (e.g., kink-resistant) as the prior art braided sheaths, but sheath 25 may be split relatively easily along slit 46 of seam 44 by application of a circumferential force thereto, thereby allowing the sheath to be removed from vessel 22. Advantageously, splitting the sheath as described allows the removal of the sheath without having to move apparatus 48 away from the patient's body and without disconnecting the catheter from the external apparatus. Braided section 38 preferably remains intact during this procedure.

It is to be appreciated that various features of the invention which are, for clarity, described in the contexts of separate embodiments may also be provided in combination in a single embodiment. Conversely, various features of the invention which are, for brevity, described in the context of a single embodiment may also be provided separately or in any suitable subcombination. It will therefore be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

What is claimed is:

1. Apparatus for insertion into a lumen of a body of a subject, comprising a sheath, the sheath comprising:

at least one section which is reinforced by braiding, the section extending longitudinally along at least a portion of the sheath; and at least one section which does not comprise any reinforcing elements, extending longitudinally along at least the portion, wherein the at least one section which is substantially not reinforced comprises a splittable seam.

2. Apparatus according to claim 1, wherein the seam is adapted to open responsive to application of lateral tension thereto.

3. Apparatus according to claim 1, wherein the sheath is adapted to be inserted into a blood vessel.

4. A method for removing a sheath from a lumen of a body of a subject, comprising:

withdrawing the sheath from the lumen so that a segment of the sheath is outside the body, the sheath having at least one longitudinal section thereof which is reinforced by braiding, and at least one longitudinal section thereof which does not comprise any reinforcing elements; and applying tension to the non-reinforced section, so as to split the sheath longitudinally at the non-reinforced section.

5. A method according to claim 4, wherein applying the tension so as to split the sheath comprises splitting the sheath along a seam of the at least one longitudinal section which is substantially not reinforced.

* * * * *